(12) United States Patent
Klein

(10) Patent No.: US 8,053,475 B2
(45) Date of Patent: Nov. 8, 2011

(54) PREPARATION OF THE FORMAURINDIKARBOXYL ACID BASE AND ITS DERIVATIONS AND USE

(75) Inventor: Pavel Klein, Královice (CZ)

(73) Assignee: Vyzkumny Ustav Zivocisne Vyroby, V.V.I. (CZ)

( * ) Notice: Subject to any disclaimer, the term of this patent is extended or adjusted under 35 U.S.C. 154(b) by 0 days.

(21) Appl. No.: 12/879,483

(22) Filed: Sep. 10, 2010

(65) Prior Publication Data

US 2011/0009490 A1 Jan. 13, 2011

Related U.S. Application Data

(62) Division of application No. 12/103,783, filed on Apr. 16, 2008.

(30) Foreign Application Priority Data

Dec. 4, 2007 (CZ) .................................. 2007-851

(51) Int. Cl.
  *A61K 31/19* (2006.01)
  *A61K 31/60* (2006.01)
(52) U.S. Cl. ........ 514/568; 514/570; 514/557; 514/159; 424/404

(58) Field of Classification Search .................. 514/568, 514/570, 557, 157; 424/404
See application file for complete search history.

(56) References Cited

U.S. PATENT DOCUMENTS 4,002,745 A * 1/1977 Bernstein et al. ............. 514/159

OTHER PUBLICATIONS

Abdel-Ghaffer et al., Parisitol. Res., 1990, vol. 76, pp. 440-443.*
Dalloul et al, Avian diseases, vol. 49, 2005, pp. 1-8.*
Bryan et al. An overview of cryptosporidiosis, 2007, retrieved from the internet on Dec. 27, 2010, URL: http://www.vet.uga.edu/vpp/clerk/bryan/index.php, pp. 1-6.*
Gilson et al. , The Body, the complete HIV/AIDS resource, 1996, pp. 1-8.*
Whiteside et al , Am. J. Trop. Med. Hyg. vol. 33 (6), 1984, pp. 1065-1072.*

* cited by examiner

*Primary Examiner* — Jeffrey S. Lundgren
*Assistant Examiner* — Savitha Rao
(74) *Attorney, Agent, or Firm* — Ostrolenk Faber LLP

(57) ABSTRACT

A pharmaceutical composition comprising at least 0.1 μmol of formaurindicarboxylic acid or its derivatives in 1 kg of pharmaceutically acceptable carrier. The pharmaceutical composition of claim 1 wherein the composition is in the form of solution prepared using aqueous alcali or water.

1 Claim, 1 Drawing Sheet

PREPARATION OF THE FORMAURINDIKARBOXYL ACID BASE AND ITS DERIVATIONS AND USE

CROSS REFERENCE TO RELATED APPLICATIONS

Figure 1:
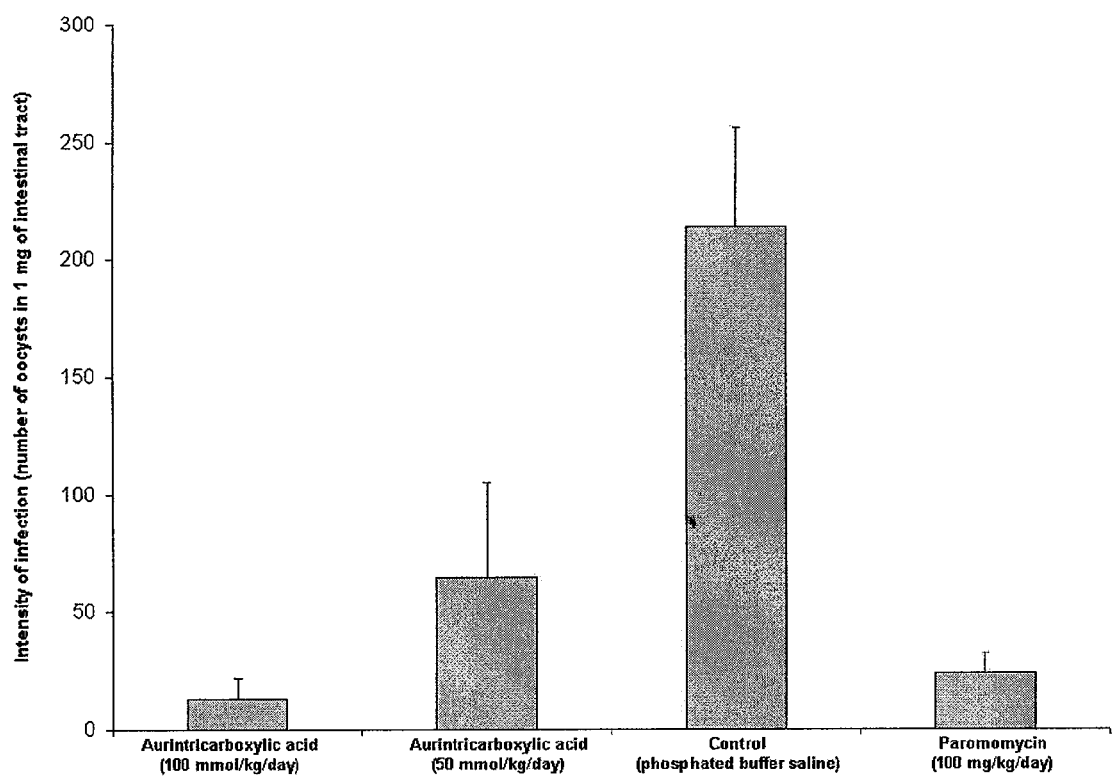

This application is a divisional of U.S. application Ser. No. 12/103,783, filed Apr. 16, 2008, by Ing. Pavel KLEIN, entitled PREPARATION ON THE FORMAURINDICARBOXYLIC ACID BASE AND ITS DERIVATES AND THEIR USE, which claims the benefit of Czech Republic Application No. PV 2007-851, filed Dec. 4, 2007, the disclosures of which have been incorporated herein by reference.

FIELD OF INVENTION

The present invention relates to the preparation for prevention and therapy of coccidial infections, against which formaurindicarboxylic acid and its derivates are used as highly effective anticoccidial agent.

BACKGROUND OF THE INVENTION

Coccidia parasites infect a wide range of animal species, especially farm animals where they cause significant economic losses due to mortality, morbidity, lower performance and extra costs associated with treatment and prevention. The most common coccidia belong to the genus *Eimeria*, which infect birds and mammals. Other common coccidian genera found in farm animals are *Cryptosporidium* and *Isospora*.

*Cryptosporidium parvum* typically infects the small intestine of neonates of ruminants, and is also human pathogen. In the human population, *C. parvum* and the genetically closely related species *C. hominis* are mostly diagnosed in individuals with a compromised immune system, mostly people with AIDS, where they cause profuse, long-lasting watery diarrhea. In immunocompetent people *Cryptosporidium* causes enteritis and diarrhea which is self-limiting. Nevertheless, severe diarrhea and dehydration may cause serious complications in children and in older persons.

Today, two different approaches for the control of coccidioses are used: 1) vaccination, and 2) administration of coccidiostats and anticoccidials. Vaccination against some Eimeria species is commercially available for use in poultry. Other animals must be treated by anticoccidials covering now all known coccidian species. A problem accompanying the use of these drugs, which were mostly synthesized in 1950s-70s, is the risk of resistancy and the need to rotate treatment programs. Also, residuality of these drugs represents a risk if drugs enter the food chain.

Treatment of cryptosporidial infections is problematic due to the lack of reliable drugs, as well as by the limitations associated with immunotherapy (Harp et Goff, 1995; Jenkins, 2004). People may be treated with paromomycin, and by azithromycin, nitazoxanide or lehrazuril, drugs with a limited efficacy against cryptosporidiosis (Blanshard et al., 1997; Giacometti et al., 1998). In animals, the only registered drug is halofuginone-lactate.

Because of these problems, it is evident that there is a need to find new highly effective anticryptosporidial drugs which should not be toxic to the host and should not leave any residual.

Background Publications Include:

Blanshard C, Shanson D C, Gazzard B G: Pilot studies of azithromycin, letrazuril and paromomycin in the treatment of cryptosporidiosis. Int J STD AIDS 1997; 8(2):124-9

Giacometti A, Burzacchini F, Cirioni O, Barchiesi F, Dini M, Scalise G: Efficacy of treatment with paromomycin, azithromycin, and nitazoxanide in a patient with disseminated cryptosporidiosis. Eur J Clin Microbiol Infect Dis, 1998; 18:885-889.

Harp J A, Goff J P: Protection of calves with a vaccine against *Cryptosporidium parvum*. J Parasitol. 1995; 81(1):54-7.

Jenkins M C: Present and future control of cryptosporidiosis in humans and animals. Expert Rev Vaccines. 2004; 3(6):669-71

Liang F, Huang Z, Lee S Y, Liang J, Ivanov M I, Alonso A, Bliska J B, Lawrence D S, Mustelin T, Zhang Z Y: Aurintricarboxylic acid blocks in vitro and in vivo activity of YopH, an essential virulent factor of Yersinia pestis, the agent of plague. J Biol Chem. 2003; 278(43):41734-41.

Okada N, Koizumi S: A neuroprotective compound, aurin tricarboxylic acid, stimulates the tyrosine phosphorylation cascade in PC12 cells. J Biol Chem. 1995; 270(27):16464-9.

Owens M R, Holme S.: Aurin tricarboxylic acid inhibits adhesion of platelets to subendothelium. Thromb Res. 1996; 81(2):177-85.

Tzipori S: Cryptosporidiosis: laboratory investigations and chemotherapy. Adv Parasitol. 1998; 40:187-221

DETAILED DESCRIPTION OF PREFERRED EMBODIMENTS OF THE INVENTION

The above mentioned drawbacks of existing treatments are eliminated using a preventive and therapeutical treatment against coccidioses by the invention, wherein 1 kg of suitable carrier contains at least 0.1 µmol of formaurindicarboxylic acid and its derivates represented by the following formula:

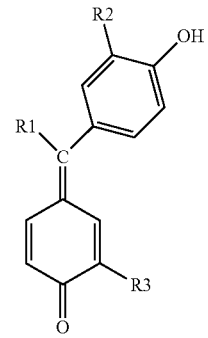

in which R1-R3 mean

| | R1 | R2 | R3 |
|---|---|---|---|
| Formaurindi-carboxylic acid | H | COOH | COOH |
| Formaurindi-carboxylates (salts of formaurindi-carboxylic acid) | H | COO$^-$ | COO$^-$ |
| Aurintri-carboxylic acid | 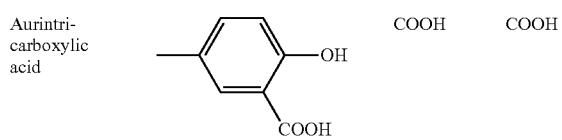 | COOH | COOH |

-continued

| | R1 | R2 | R3 |
|---|---|---|---|
| Aurintri-carboxylates (salts of aurintri-carboxylic acid) | (structure: phenyl with OH and COO⁻) | COO⁻ | COO⁻ |
| Aluminon | (structure: phenyl with OH and COO⁻NH₄⁺) | COO⁻ NH₄⁺ | COO⁻ NH₄⁺ |

The carrier can be any suitable material, including aqueous alcalic solution or water.

The above mentioned derivative compounds are known and the most important of them, aurintricarboxylic acid (ATA) has been described for its strong biological effects on organisms. ATA is a potent inhibitor of endonuclease activity; namely DNAase I, RNAase A, S1 nuclease, exonuclease III or restriction endonucleases Sal I, Bam HI, Pst I and Sma I (Hallick et al. 1977). Other biological properties of ATA are based on its ability to stimulate tyrosin phosphorylation (Okada and Koizumi, 1995). ATA also inhibits von Willebrand factor binding to platelets and thus prevents blood coagulation (Owens and Holme, 1996). Antimicrobial properties of ATA have been also described as this compound suppresses pathogenicity of *Yersinia* (Liang et al., 2003).

Interestingly, the use of aurintricarboxylic acid for antiprotozoal treatment has not been described to date. In the literature, these compounds are described as aurintricarboxylic acid (CAS# 4431-00-9), triammonium salt of aurintricarboxylic acid, aluminon (CAS# 569-58-4), and as formaurindicarboxylic acid (CAS# 621051-06-3).

Because of the mechanism of action of these compounds, there is reason to believe that may also be used against other protozoal infections, if administered in an appropriate formulation.

EXAMPLE

In vivo model designed by Tzipori (1998) was used in following modification: Three-day-old, SPF C57B1/6 baby mice (Velaz, Czech Republic) were randomly assigned to groups of 8-9 mice. The baby mice were caged with their mother in sterile microisolators equipped with filter tops under standard conditions. 4-day-old mice were orally infected with 100 000 oocysts and the treatment was initiated at the same time; the daily dose of aurintricarboxylic acid 50 and 100 mmol/kg/day was divided into 2 equal portions and orally administered in 12-hr intervals. A control group received phosphate buffer saline, and paromomycin (100 mg/kg/day) was used as positive control. ATA was prepared fresh before each use by dissolving the drug in aqueous solution of sodium hydroxide or potassium hydroxide at a molar ratio of 1:3 (ATA:NaOH), or in dimethylsulfoxide. The treatment was continued for 8 days and it was tolerated without any visible signs of toxicity. Intensity of infection was expressed as the number of oocysts in homogenized intestinal tract in the 9th day after infection. The experiment was repeated between 2006 and 2007 and always gave very similar results. FIG. 1 shows results of the last experiment where ATA was dissolved in sodium hydroxide.

There is reason to believe that ATA is also effective against other coccidians (including *Eimeria, Isospora*).

Structure of formaurindicarboxylic acid and its derivates of the structure:

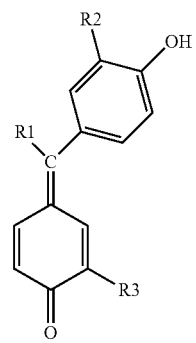

In which R1-R3 mean

| | R1 | R2 | R3 |
|---|---|---|---|
| Formaurindicarboxylic acid | H | COOH | COOH |
| Formaurindicarboxylates (salts of formaurindicarboxylic acid) | H | COO⁻ | COO⁻ |
| Aurintricarboxylic acid | (structure: phenyl with OH and COOH) | COOH | COOH |
| Aurintricarboxylates (salts of aurintricarboxylic acid) | (structure: phenyl with OH and COO⁻) | COO⁻ | COO⁻ |
| Aluminon | (structure: phenyl with OH and COO⁻NH₄⁺) | COO⁻ NH₄⁺ | COO⁻ NH₄⁺ |

The inihibition aurintricarboxylic acid on experimental *Cryptosporidium parvum*-infection in suckling C57B16 mice is graphed in FIG. 1.

What is claimed:

1. A method for treating cryptosporidiosis said subject to treat cryptosporidiosis comprising the steps of:
   providing a composition comprising at least one of formaurindicarboxylic acid; aurintricarboxylic acid; salts of formaurindicarboxylic acid; salts of aurintricarboxylic acid; and aluminon; and administrating an effective amount of said composition to in a subject in need of such treatment, the method.

* * * * *